United States Patent
Laufer

(10) Patent No.: US 8,790,360 B2
(45) Date of Patent: Jul. 29, 2014

(54) METHODS AND DEVICES FOR DISSECTING TISSUE

(75) Inventor: Michael D. Laufer, Menlo Park, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 958 days.

(21) Appl. No.: 12/427,853

(22) Filed: Apr. 22, 2009

(65) Prior Publication Data

US 2009/0264910 A1 Oct. 22, 2009

Related U.S. Application Data

(60) Provisional application No. 61/047,080, filed on Apr. 22, 2008.

(51) Int. Cl.
*A61B 17/32* (2006.01)

(52) U.S. Cl.
USPC .......................................... 606/169

(58) Field of Classification Search
CPC ........... A61B 2017/00367; A61B 2017/00389; A61B 2017/00398
USPC ......... 606/45, 49, 169, 170, 171, 180; 604/22
See application file for complete search history.

(56) References Cited

U.S. PATENT DOCUMENTS

| | | | | |
|---|---|---|---|---|
| 5,304,115 A | * | 4/1994 | Pflueger et al. | 604/22 |
| 6,027,460 A | * | 2/2000 | Shturman | 600/585 |
| 6,494,888 B1 | | 12/2002 | Laufer et al. | |
| 6,663,639 B1 | | 12/2003 | Laufer et al. | |
| 6,976,969 B2 | | 12/2005 | Messerly | |
| 7,347,863 B2 | | 3/2008 | Rothe et al. | |
| 2002/0183768 A1 | * | 12/2002 | Deem et al. | 606/151 |
| 2004/0147934 A1 | * | 7/2004 | Kiester | 606/80 |
| 2004/0225305 A1 | | 11/2004 | Ewers et al. | |
| 2005/0251162 A1 | * | 11/2005 | Rothe et al. | 606/153 |
| 2007/0218083 A1 | | 9/2007 | Brooks | |
| 2009/0005797 A1 | | 1/2009 | Laufer et al. | |
| 2009/0018391 A1 | | 1/2009 | Laufer et al. | |
| 2009/0264902 A1 | | 10/2009 | Laufer | |

OTHER PUBLICATIONS

International Search Report & Written Opinion, PCT/US2009/041362, Mailed Oct. 26, 2010, 8 pages.
International Search Report & Written Opinion, PCT/US2009/041369, Mailed Oct. 26, 2010, 7 pages.
International Search Report & Written Opinion, PCT/US2009/014362, Mailed Jun. 8, 2009, 11 pages.

* cited by examiner

*Primary Examiner* — Thomas McEvoy
(74) *Attorney, Agent, or Firm* — Mintz Levin Cohn Ferris Glovsky and Popeo, P.C.

(57) ABSTRACT

Methods and devices are provided for dissecting tissue. In one embodiment, a surgical device can include an elongate shaft configured to be introduced into a body of a patient. A transducer coupled to the elongate shaft can be configured to deliver mechanical energy to the elongate shaft, e.g., axially along the elongate shaft, to rotate, vibrate, and/or flex the elongate shaft to facilitate dissection of tissue adjacent at least a leading end or a distal end of the elongate shaft. In some embodiments the elongate shaft can include at least two coaxial coils, and the transducer can be configured to move at least one of the coaxial coils to facilitate tissue dissection using the elongate shaft.

21 Claims, 4 Drawing Sheets

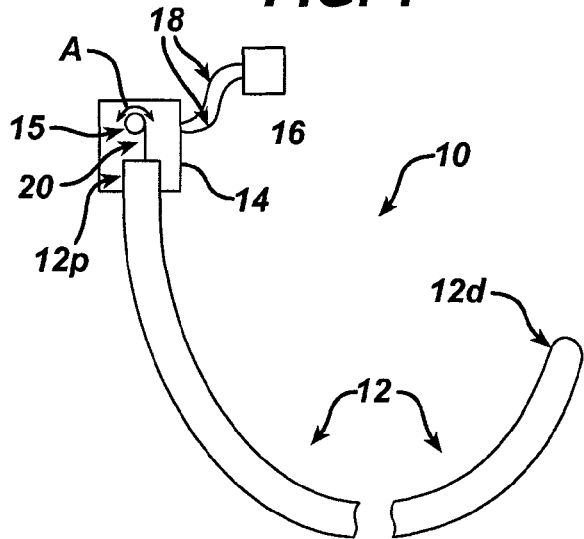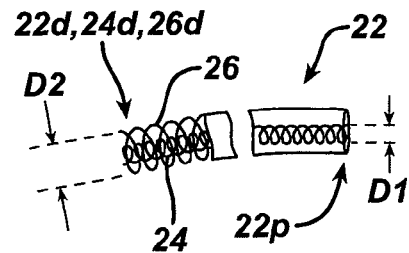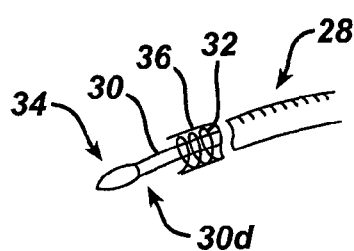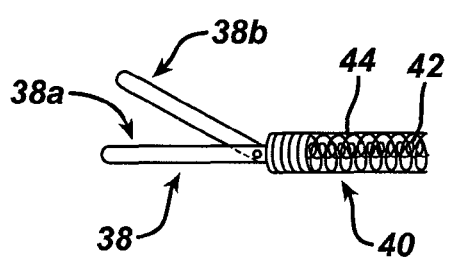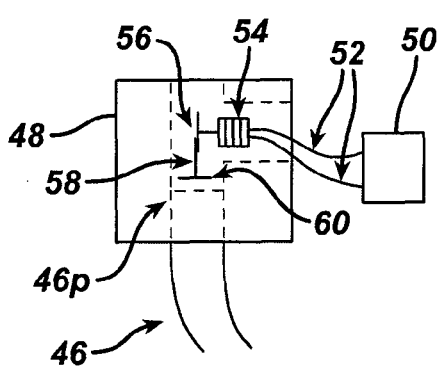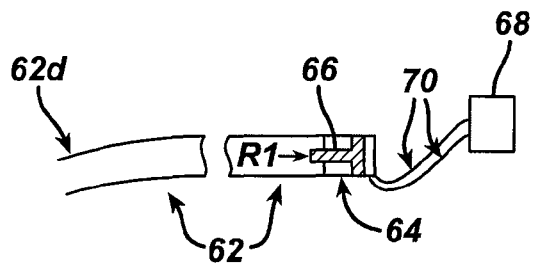

METHODS AND DEVICES FOR DISSECTING TISSUE

CROSS REFERENCE TO RELATED APPLICATIONS

The present application claims the priority of U.S. Provisional Application Ser. No. 61/047,080 filed Apr. 22, 2008 entitled "Device For Low-Frequency Dissection Around A Bodily Organ," which is herein incorporated by reference in its entirety.

FIELD OF THE INVENTION

The present invention relates to methods and devices for dissecting tissue.

BACKGROUND OF THE INVENTION

Laparoscopic surgery has greatly reduced the size and scope of incisions made in a patient and resulted in reduced morbidity and mortality rates. However, even with the reductions in the size and extent of incisions as a result of laparoscopic surgery, complications in and during surgical procedures remain. A technique that is developing to further reduce surgical complications is to work through a natural orifice such as the mouth, to access the stomach, where a hole is made through the stomach wall, to gain access to the inside of the abdominal space outside of the stomach. This NOTES approach, or natural orifice transenteric surgery, allows scarless surgical procedures with faster recovery, fewer complications, and less pain.

Stomach tissue often needs surgical treatment to treat fistulas and to close trans-gastric incisions to stop stomach fluids from leaking from the stomach to surrounding tissue and to stop infectious matter from spreading from or to the stomach tissue. Other stomach treatments include stomach reduction procedures for obese patients. Traditionally, physicians have placed devices laparoscopically on the external surface of the gastric wall to create a restricted stomach capacity. Another traditional procedure for stomach reduction includes a laparoscopic procedure in which surgeons protrude into the abdomen from the exterior of the patient and staple the stomach into a smaller volume. This restriction creates a pouch inside the stomach which fills quickly when food is ingested and assists in generating a sensation of being full. However, these procedures have drawbacks such as complications from port punctures of the stomach, large incisions, substantial recovery time, expense, lost productive work time, infection, and the like. Further, the incision required by the current surgical procedures including laparoscopy, include a morbidity and mortality rate that can be reduced by reducing or eliminating the need for an incision by approaching the surgical site through endoluminal procedures.

Thus, there is a need for devices and methods which allow surgical procedures to be performed laparoscopically while reducing or eliminating the need for an incision.

SUMMARY OF THE INVENTION

The present invention generally provides methods and devices for dissecting tissue, particularly using a distal end of a surgical tool when it is positioned in a patient and located remote from a surgeon or other operator of the tool. In one embodiment, a surgical device is provided that includes an elongate shaft configured to be inserted into a body, and a transducer configured to deliver mechanical energy to the elongate shaft to facilitate tissue dissection by a leading end of the elongate shaft.

In some embodiments, the transducer can be configured to deliver mechanical energy axially along the elongate shaft. The transducer can be configured to deliver mechanical energy to alternately rotate the elongate shaft around a longitudinal axis of the elongate shaft in a first direction and in a second direction opposite to the first direction. Alternatively or in addition, the transducer can be configured to deliver mechanical energy to vibrate the elongate shaft.

The device can vary in any other number of ways. For example, the elongate shaft can have a pair of movable jaws at a distal end thereof. The transducer can be configured to deliver mechanical energy to the elongate shaft to actuate the movable jaws. For another example, the elongate shaft can include a longitudinal first coil coaxial with a longitudinal second coil. The transducer can be configured to deliver mechanical energy to the elongate shaft to alternately rotate the elongate shaft in a first direction to tighten the first coil and loosen the second coil and in a second direction to loosen the first coil and tighten the second coil. Alternatively or in addition, the transducer can be configured to deliver mechanical energy to the elongate shaft to longitudinally vibrate the first coil relative to the second coil.

In another embodiment, a surgical device is provided that includes an elongate body including a first elongate coil having a first inner passageway, and a second elongate coil disposed in the first inner passageway. The device also includes a transducer configured to provide mechanical energy to the elongate body to move at least one of the first elongate coil and the second elongate coil to facilitate tissue dissection by a distal end of the elongate body.

The device can have any number of variations. For example, helices of the first elongate coil and the second elongate coil can twist in opposite directions. The transducer can be configured to alternately rotate the elongate body in a first direction to tighten the first elongate coil and loosen the second elongate coil and in a second direction to loosen the first elongate coil and tighten the second elongate coil. For another example, distal ends of the first and second elongate coils can be attached together. The transducer can be configured to longitudinally move the second elongate coil relative to the first elongate coil to flex a distal end of the elongate body. For yet another example, a first distal cutting tip can be attached to the first elongate coil and a second distal cutting tip can be attached to the second elongate coil.

In another aspect, a surgical method is provided that includes advancing an elongate member into a body of a patient, and actuating a transducer coupled to the elongate member to deliver mechanical energy to the elongate member to facilitate tissue dissection. The method can vary in any number of ways. For example, actuating the transducer can include delivering mechanical energy axially along the elongate member.

In some embodiments, the elongate member can include a first coil disposed in a second coil, and actuating the transducer can include delivering mechanical energy to at least one of the first and second coils to move at least one of the first and second coils to dissect tissue with a distal end of the elongate member. Delivering mechanical energy to at least one of the first and second coils ca include alternately axially rotating the elongate member in a first direction to tighten the first coil and loosen the second coil and in a second direction to tighten the second coil and loosen the first coil. Alternatively or in addition, delivering mechanical energy to at least one of the first and second coils can include longitudinally vibrating the first coil relative to the second coil. A pair of movable jaws can optionally be disposed at the distal end of the elongate member, and delivering mechanical energy to at least one of the first and second coils can cause the movable jaws to move and cut tissue.

BRIEF DESCRIPTION OF THE DRAWINGS

The invention will be more fully understood from the following detailed description taken in conjunction with the accompanying drawings, in which:

FIG. 1 is a partial cutaway perspective view of one embodiment of a dissection device;

FIG. 2 is a partial side transparent view of one embodiment of an elongate shaft of a dissection device including two coaxial coils;

FIG. 3 is a partial side transparent view of one embodiment of an elongate shaft of a dissection device including two coaxial coils and a distal cutting tip in the form of a tapered cone;

FIG. 4 is a partial side transparent view of one embodiment of an elongate shaft of a dissection device including two coaxial coils and a distal cutting tip in the form of movable jaws;

FIG. 5 is a partial cutaway perspective view of another embodiment of a dissection device;

FIG. 6 is a partial cutaway perspective view of one embodiment of a dissection device with an elongate shaft of the dissection device in a resting position;

DETAILED DESCRIPTION OF THE INVENTION

Figure 7:
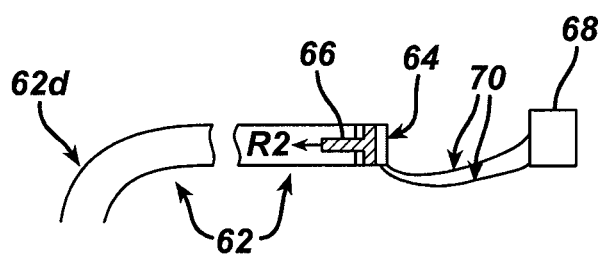
FIG. 7 is a partial cutaway perspective view of the dissection device of FIG. 6 with the elongate shaft in a flexed position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for dissecting tissue, especially when a distal end of the device is remote from a proximal end that is controlled by a surgeon or other operator. In one embodiment, a surgical device can include an elongate shaft configured to be introduced into a body of a patient. A transducer coupled to the elongate shaft can be configured to deliver mechanical energy to the elongate shaft, e.g., axially along the elongate shaft, to rotate, vibrate, and/or flex the elongate shaft to facilitate dissection of tissue adjacent at least a leading end or a distal end of the elongate shaft. In this way, when the surgical device advances through a body of a patient, the transducer can provide energy to the elongate shaft to help the device dissect tissue that the leading end or distal end of the elongate shaft encounters that could otherwise slow or prevent advancement of the device through the body. In some embodiments the elongate shaft can include at least two coaxial coils, and the transducer can be configured to move at least one of the coaxial coils to facilitate tissue dissection using the elongate shaft.

A person skilled in the art will appreciate that while the methods and devices are described in connection with endoscopic procedures in which the surgical instruments are delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. A person skilled in the art will also appreciate that the methods and devices disclosed herein can be used with any surgical tool, such as a scoping device, having a cannula or other working channel through which the shaft of a surgical instrument can be advanced and that is configured to be inserted into a body, such as through a natural orifice, through a puncture hole formed in tissue, and in any other way appreciated by a person skilled in the art. Non-limiting examples of a scoping device include an endoscope, a laparoscope, and a colonoscope.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations and generally refers to a property that enables a material or an object to deform to some extent without failing. In an exemplary embodiment, the device or at least portions thereof are composed of at least one biocompatible and flexible material, e.g., plastic, titanium, stainless steel, a shape memory material, etc.

FIG. 1 illustrates a dissection device 10 configured to have at least a portion thereof introduced into a body of a patient and to dissect tissue in the body. In an exemplary embodiment, the dissection device 10 includes an elongate member, elongate shaft, or elongate body 12 and a transducer 14 located at a proximal end 12p of the elongate shaft 12. Generally, the transducer 14 can be configured to deliver mechanical energy to the elongate shaft 12, such as by receiving electrical energy, converting the electrical energy to mechanical energy, and delivering the mechanical energy to the elongate shaft 12 via a connector rod 20 or any other mechanical coupling mechanism, as will be appreciated by a person skilled in the art. As discussed further below, the mechanical energy delivered to the elongate shaft 12 can rotate, vibrate, and/or flex at least a portion of the elongate shaft 12 and can be delivered as a mechanical force to at least a distal end 12d of the elongate shaft 12, which can help the elongate shaft 12 dissect tissue adjacent its distal end 12d. Although the transducer 14 in this illustrated embodiment is configured to receive electrical energy from a power supply 16 coupled to the transducer 12 via one or more leads 18, the transducer 14 can receive and/or generate electrical energy in any wired and/or wireless way, as will be appreciated by a person skilled in the art. Further, although the transducer 14 shown in FIG. 1 is configured to deliver mechanical energy to the elongate shaft 12 to vibrate at least a portion of the elongate shaft 12, as mentioned above and as discussed further below, in some embodiments a transducer can be configured to additionally or alternatively flex and/or rotate an elongate member, elongate shaft, or elongate body of a dissection device.

The elongate shaft 12 can have a variety of sizes, shapes, and configurations. Generally, the elongate shaft 12 can have a shape, size, and configuration that allows it to couple to the transducer 14 and to be introduced into a body of a patient. The elongate shaft 12 can be rigid, flexible, or a combination thereof, but it is preferably flexible at least along a substantial length thereof and substantially incompressible along its longitudinal length. The elongate shaft 12 can be solid as shown, or the elongate shaft 12 can be at least partially cannulated, e.g., to allow one or more surgical tools to be advanced therethrough. In an exemplary embodiment, the elongate shaft 12 can be flexible to allow it to be introduced into a body of a patient, e.g., in a minimally invasive technique, such as through a natural orifice and/or through a working channel of a flexible scoping device (or through an auxiliary channel of a flexible scoping device) having at least its distal end disposed in a body. A person skilled in the art will appreciate that having a flexible shaft indicates that at least a portion of the elongate shaft 12 is composed of one or more flexible materials.

The elongate shaft 12 can have any longitudinal length, but its length is preferably long enough to allow the shaft's proximal end 12p to be positioned outside a body of a patient when the shaft's distal end 12d and at least a portion of the shaft's longitudinal length is disposed in a body.

In an exemplary embodiment, the elongate shaft 12 can be substantially cylindrical to help the elongate shaft 12 pass smoothly into a body. The elongate shaft 12 can have any constant or varying shape along its longitudinal length, and its diameter can be uniform or non-uniform along the elongate shaft's longitudinal length. In an exemplary embodiment, the elongate shaft 12 can have a substantially uniform diameter along its longitudinal length except in its distal portion 30, which can distally taper and have a smaller diameter than a proximal longitudinal length of the shaft 12 to help the shaft's distal end 12d penetrate tissue.

The elongate shaft 12 can include a singular tubular or solid elongate member, or the elongate shaft 12 can include one or more elongate coils extending along at least a partial longitudinal length of the shaft 12. The one or more coils can optionally be disposed in an outer sheath, as will be appreciated by a person skilled in the art.

FIG. 2 illustrates one exemplary embodiment of an elongate member, elongate shaft, or elongate body 22 that includes first and second coaxial coils 24, 26 with the first or inner coil 24 disposed in the second or outer coil 26. The elongate shaft 22 can be configured and used similar to the shaft 12 discussed above and can be coupled to a transducer configured to deliver mechanical energy to the elongate shaft 22. Although only two coaxial coils are illustrated in FIG. 2, the elongate shaft 22 can include any number of coaxial coils.

The first and second coils 24, 26 can have a variety of sizes, shapes, and configurations. As shown in this embodiment, the first and second coils 24, 26 can each be substantially cylindrical with the second coil 26 having a second diameter D2 greater than a first diameter D1 of the first coil 24 to allow the first coil 24 to be disposed within an inner passageway of the second coil 26. The first and second diameters D1, D2 can be uniform or non-uniform along their respective first and second coils 24, 26. The first coil 24 can optionally taper at its distal end 24d, as illustrated in FIG. 2, which as discussed further below can help flex a distal end 22d of the elongate shaft 22. Although not shown in this embodiment, the distal end 24d of the first coil 24 can optionally be attached to a distal end 26d of the second coil 26, which also as discussed further below can help flex the elongate shaft's distal end 22d.

The first and second coils 24, 26 can have any number of coils having any pitch. The first and second coils 24, 26 can be configured with relatively small pitches such that the shaft 22 can be substantially incompressible along its longitudinal length. In an exemplary embodiment in which an elongate shaft includes at least two elongate coils, at least two of the coils can twist in opposite directions. As illustrated in this embodiment, the first and second coils 24, 26 can twist in opposite directions with the first coil 24 twisting in a first direction, e.g., clockwise, and the second coil 26 twisting in a second, opposite direction, e.g., counterclockwise. As discussed further below, having opposed helices can help facilitate transmission of torque from a transducer from a proximal end 22p of the shaft 22 to the distal end 22d of the shaft 22.

Although the elongate shafts 12, 22 in FIGS. 1 and 2 do not have an accessory attached to their respective distal ends 12d, 22d, a dissection device can have an accessory removably or fixedly coupled to a distal end of its an elongate member, elongate shaft, or elongate body. As illustrated in one embodiment in FIG. 3, an elongate member, elongate shaft, or elongate body 28 can include first and second coaxial coils 30, 32 and can have an accessory 34 at a distal end 28d of the elongate shaft 28. The accessory 34 can include a cutting tip, e.g., a distally tapered cone as shown, that can help facilitate dissection of tissue, although the accessory 34 can include a cutting tip of any shape configured to facilitate tissue dissection. The accessory 34 can be attached to the elongate shaft 28 in any way, such as by being fixedly attached to or integrally formed with a distal end 30d of the first or inner coil 30. As shown, the accessory 34 can at least partially extend distally beyond a distal end 32d of the second or outer coil 32 to allow the accessory 34 to lead the elongate shaft 28 when the shaft 28 is advanced through tissue. FIG. 3 also illustrates an outer sheath 36 disposed over the first and second coils 30, 32 configured to help protect the coils 30, 32 and help prevent the elongate shaft 28 from snagging on tissue or other material.

FIG. 4 illustrates another embodiment of a dissection device having an accessory 38 in the form of a scissor-like tip including a pair of movable first and second distal cutting tips configured to cut tissue at a distal end of the device's elongate member, elongate shaft, or elongate body 40. The distal cutting tips can have a variety of configurations, but as shown in this embodiment they can include a pair of jaws 38a, 38b having a sharp inner edge. A person skilled in the art will appreciate that one or both of the jaws 38a, 38b can be configured to move between an open position (illustrated in FIG. 4) and a closed position to cut tissue. A person skilled in the art will also appreciate that one or both of the jaws 38a, 38b can be configured to move relative to the other jaw. The jaws 38a, 38b can be attached in any way to the elongate shaft 40. As in the illustrated embodiment the first jaw 38a can be fixedly or removably attached to a first or inner coil 42, and the second jaw 38b can be fixedly or removably attached to a second or outer coil 44. The first and second coils 42, 44 can be coaxial and configured similar to the coaxial coils of FIGS. 2 and 3.

Referring again to FIG. 1, the elongate shaft 12 can be coupled to the transducer 14 in any way, as will be appreciated by a person skilled in the art, such as by being mechanically coupled via the connector rod 20 extending between the transducer 14 and the distal end 12d of the elongate shaft 12. The connector rod 20 can have a variety of sizes, shapes, and configurations, and in an exemplary embodiment can be a substantially cylindrical rigid member configured to help deliver mechanical force from the transducer 14 to the elongate shaft 12.

As shown in the embodiment illustrated in FIG. 1 the transducer 14 can be configured to deliver mechanical energy axially along the elongate shaft 12 to rotationally vibrate the elongate shaft 12, although as mentioned above, the transducer 14 can be configured to rotate, vibrate, and/or flex the elongate shaft 12. To deliver mechanical energy to the elongate shaft 12, an eccentric wheel 15 coupled to the transducer 14 can be configured to alternately rotate in first and second opposite directions, e.g., clockwise and counterclockwise as shown by directional arrow A, when the power supply 16 delivers electrical power to the transducer 14 over the leads 18. The frequency of the vibration can be varied or fixed and can be at any audible or sub-ultrasonic frequency, e.g., in a range of about 10 to 10,000 vibrations per second. Wavelength and stroke of the vibration can also be varied, e.g., in a range of about 0.1 to 1 mm. The rod 20 can be coupled at one terminal end to the eccentric wheel 15 and at another terminal end to the elongate shaft 12 such that when the eccentric wheel 15 alternately moves in the first and second directions, the rod 20 can also alternately move in the first and second directions, thereby translating the movement to the elongate shaft 12. In some embodiments the eccentric wheel 15 can be configured to move in only one of the first and second directions, thereby rotating the elongate shaft 12 rather than vibrationally rotating the shaft 12.

In use, the transducer 14 can be actuated, e.g., by turning the transducer 14 on or otherwise activating the transducer 14, to convert electrical power received from the power supply 16 and vibrationally rotate the shaft 12 and facilitate dissection of tissue therewith. The transducer 14 can be configured to be continuously actuated to continuously deliver mechanical energy to the shaft 12. Alternatively or in addition, the transducer 14 can be configured to be selectively actuated to selectively deliver mechanical energy to the shaft 12, such as when the shaft 12 encounters resistance when being moved through a body of a patient, thereby indicating that tissue can be obstructing its path.

If the elongate shaft 12 includes at least two coaxial coils with at least two of the coils twisting in opposite directions, turning the eccentric wheel 15 in one of the first and second directions can tighten at least one of the coils and loosen at least one of the other of the coils, while turning the eccentric wheel 15 in the other of the first and second directions can cause the opposite. In other words, turning the eccentric wheel 15 can alternately rotate the elongate shaft around a longitudinal axis of the elongate shaft in the first and second directions to rotationally vibrate the elongate shaft. The coils can thereby function as one unit and transmit torque from a proximal end of the elongate shaft to a distal end of the elongate shaft.

FIG. 5 illustrates another embodiment of a dissection device including an elongate member, elongate shaft, or elongate body 46 and a transducer 48 located at a proximal end 46p of the elongate shaft 46. The elongate shaft 46 and the transducer 48 can be used and configured similar to those discussed above. However, in this illustrated embodiment, the transducer 48 can be configured to deliver mechanical energy to the elongate shaft 46 to rotate the elongate shaft 46. The transducer 48 can be coupled to a power supply 50 via one or more leads 52. When the transducer 48 is actuated, e.g., by providing power from the power supply 50 to the transducer 48 via the one or more leads 52, a motor 54 of the transducer 46 can be configured to rotate an eccentric wheel 56 of the transducer 46 in at least one direction, e.g., clockwise and/or counterclockwise. The motor 54 can be configured to rotate the eccentric wheel 56 at any speed. The eccentric wheel 56 can be coupled to a rod 58 with one end of the rod 58 coupled to the eccentric wheel 56 and another end of the rod 58 coupled to a plate 60 configured to alternately contact the elongate shaft 46. The eccentric wheel 56 can be configured to move the rod 58 up and down when the eccentric wheel 56 rotates, which can cause the plate 60 to repeatedly impact the elongate shaft 46, thereby vibrating the elongate shaft 46. A coupling can hold the elongate shaft 46 as it is impacted by the plate 60. As mentioned above, the frequency of the vibration can be varied or fixed and can be at any audible or sub-ultrasonic frequency, e.g., in a range of about 10 to 10,000 vibrations per second, and wavelength and stroke of the vibration can also be varied, e.g., in a range of about 0.1 to 1 mm.

Another embodiment of a transducer configured to vibrate an elongate shaft 62 is illustrated in FIGS. 6 and 7. The transducer can include a housing 64 and a plunger 66 disposed in the housing 64. The housing 64 and the plunger 66 can have a variety of configurations, but in an exemplary embodiment, the housing 64 can include an electromagnetic coil, and the plunger 66 can include a fixed magnet in the form of a solenoid. The housing 64 can be coupled to a power supply 68 via one or more leads 70. When the transducer is actuated, e.g., by supplying power from the power supply 68 to the housing 64, the housing 64 can be configured to move the plunger 66 in a back and forth motion, e.g., alternately move the plunger 66 in opposite directions such as up and down. The plunger 66 can be coupled to a proximal end of the elongate shaft 62, thereby delivering mechanical energy to the elongate shaft 62 that can be transmitted along a longitudinal length of the shaft 62 to move the elongate shaft 62 in a back and forth axial motion to vibrate the elongate shaft 62.

The plunger 66 can be coupled to the elongate shaft 62 in any way, but in the illustrated embodiment the elongate shaft 62 includes at least two coaxial coils, and the plunger 66 can be coupled to an inner coil disposed in an outer coil. The inner coil in this illustrated embodiment distally tapers and is coupled at its distal end to a distal end of the outer coil, but as mentioned above, the inner coil can have a variety of configurations. When the transducer is actuated to move the plunger 66 axially back and forth, the inner coil can correspondingly move axially back and forth to cause flexion of a distal end 62d of the elongate shaft 62. With the plunger 66 in a resting position, shown in FIG. 6, the elongate shaft 62 can also be in a resting position without any mechanical energy being applied to it by the transducer. When the plunger 66 moves in a first direction, e.g., a distal direction shown by directional arrow R1 in FIG. 7, the inner coil coupled to the plunger 66 can move in the first direction relative to the outer coil in which it is disposed. The distal end 62d of the elongate shaft 62 can thus flex and move from the resting position to a flex position, shown in FIG. 7. When the plunger 66 moves in a second direction, e.g., a proximal direction shown by directional arrow R2 in FIG. 6, the inner coil can move in the second direction relative to the outer coil, thereby moving the elongate shaft 62 to the resting position.

Figure 8:
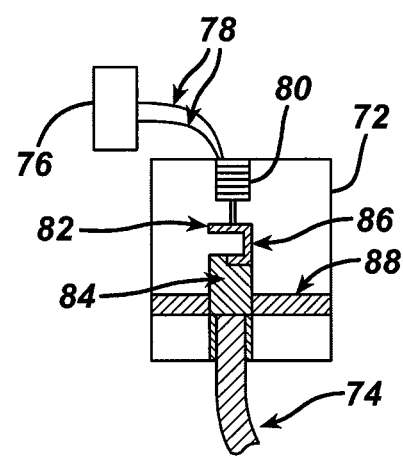
FIG. 8 is a partial cutaway perspective view of another embodiment of a dissection device.

As mentioned above, a transducer can be configured to rotate an elongate shaft of a dissection device. FIG. 8 illustrates one embodiment of a transducer configured to rotate an elongate shaft 74. The transducer can include a motor 80, a coupling 82, a cap 84, a rod 86, and a bearing 88 disposed in a housing 72 coupled to the elongate shaft 74. A power supply 76 can be configured to provide electrical energy to the transducer via one or more leads 78, which can as shown in this embodiment be coupled to the motor 80. When the transducer is actuated, the motor 80 can rotate back and forth in opposed first and second directions, which can at least partially rotate the coupling 82 coupled to the motor 80 in one or both of the first and second directions. Rotation of the coupling 82 can cause rotation of the rod 86 coupled at opposed ends to the coupling 82 and to the cap 84. The cap 84 can be coupled to a proximal end 74p of the elongate shaft 74. Rotation of the rod 86 can thus rotate the cap 84 and also rotate the elongate shaft 74. The bearing 88 can help maintain the position of the cap 84 within the housing 72.

A dissection device including a transducer and an elongate member, elongate shaft, or elongate body coupled to the transducer can optionally include a handle located adjacent to a proximal end of the elongate shaft to facilitate manipulation and handling of the device. The handle can include a power source for the transducer disposed therein and/or can include features for coupling to an energy source as well as various other features for facilitating dissection of tissue. The handle can have any configuration that allows a user to conveniently hold and operate the device. As shown in one embodiment of a dissection device 90 including a proximal handle 92 shown in FIGS. 9 and 10, the handle 92 can be located at a proximal end 94p of an elongate member, elongate shaft, or elongate body 94 having a pair of movable jaws 96 disposed at a distal end 94d thereof. The elongate shaft 92 can be configured and used similar to the elongate shafts discussed above. The handle 92 can be configured to facilitate the delivery of mechanical energy to the elongate shaft 94, e.g., include a mechanism for activating electrical energy delivery to a transducer disposed in the handle 92, such as a button or knob (not shown). Alternatively or in addition, an energy source (not shown), e.g., a battery, can be disposed within the handle 92.

Figure 9:
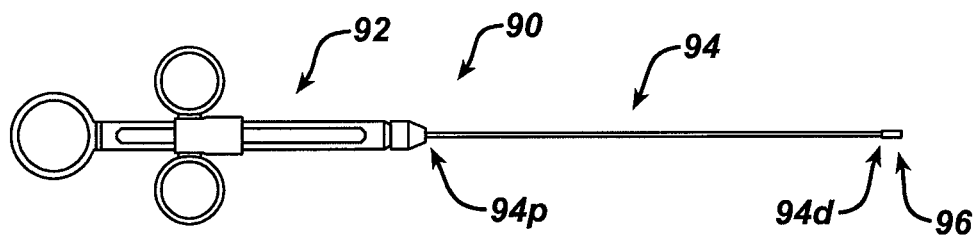
FIG. 9 is a side view of yet another embodiment of a dissection device with distal jaws of the device in a closed position.
Figure 10:
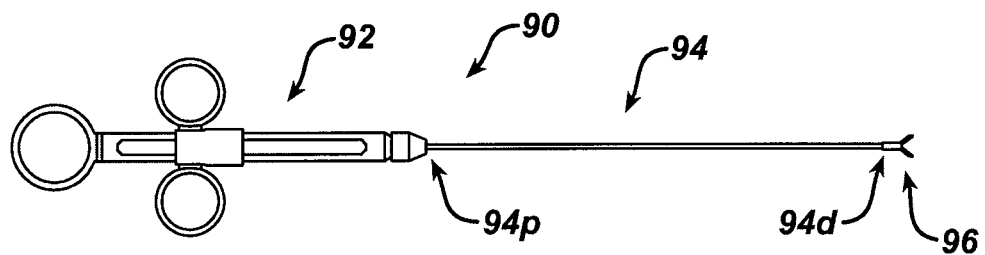
FIG. 10 is a side view of the dissection device of FIG. 9 with the distal jaws in an open position.

FIG. 9 illustrates the device 90 with the jaws 96 in a closed position, and FIG. 10 illustrates the device 90 with the jaws 96 in an open position. In an exemplary embodiment, as discussed above regarding the elongate shaft 40 and the jaws 38a, 38b of FIG. 4, one of the jaws 96 can be coupled to a first or inner coil of the elongate shaft 94, and the other one of the jaws 96 can be coupled to a second or outer coil of the elongate shaft 94. The transducer can be configured to move the inner coil relative to the outer coil when the transducer is actuated, e.g., by axially moving the inner coil similar to that discussed above regarding the transducer of FIGS. 6 and 7. In this way, the device 90 can operate similar to scissors. When the inner coil moves distally relative to the outer coil, the one of the jaws 96 attached to the inner coil can move or pivot away from the other one of the jaws 96. Similarly, when the inner coil moves proximally relative to the outer coil, the one of the jaws 96 attached to the inner coil can move or pivot toward the other one of the jaws 96. The frequency of vibration of the inner coil relative to the outer coil can control a speed at which the jaws 96 open and close.

The various embodiments of dissecting devices described herein can be used in a variety of surgical procedures. In an exemplary embodiment, an implant device can be configured to be implanted onto a lumen of a hollow body organ or conduit including the stomach, the intestine, the heart, the airway, the vein, the artery, the esophagus, the aorta, and/or the renal artery without creating an incision outside the body, wherein the implant can be configured and/or adjusted to constrict or reduce the stomach or other hollow body organ or conduit. In an exemplary embodiment of a surgical procedure applying an implant device such as a gastric band, an instrument such as an endoscope can be delivered into the stomach through the mouth or other natural orifice, a hole can be made through the stomach, a flexible wire or tube can be directed at least partially around the outside of the stomach and re-enter the stomach at or near the point of the original exit from the stomach. Additionally or alternatively, a scoping device can be positioned outside the stomach, such as by being advanced through a percutaneous abdominal access port or opening. Suitable non-limiting embodiments endoscopic devices including tissue manipulating functionality are described in more detail in U.S. Pat. No. 6,494,888 entitled "Tissue Reconfiguration" issued Dec. 17, 2002 and U.S. Pat. No. 6,663,639 entitled "Methods And Devices For Tissue Reconfiguration" issued Dec. 16, 2003, which are hereby incorporated by reference in their entireties. Although this exemplary embodiment is discussed with respect to the stomach, a person skilled in the art will appreciate that the methods and devices disclosed herein are equally applicable to other organs and/or conduits.

The tissue hole can be made by cutting, piercing, burning with radiofrequency (RF) energy directed into the tissue through a conductive tip on the wire or needle knife, or similar method as will be appreciated by a person skilled in the art. The one or more devices used to form the tissue hole can be advanced through a curved distal tip of a device such as various embodiments thereof described in more detail in previously mentioned U.S. application Ser. No. 12/427,850 entitled "Methods And Devices For Providing Direction Of Surgical Tools" filed on even date herewith.

In some embodiments, a guide wire device can be used to form the tissue hole. Generally, the guide wire device can have a distal tip that can be energized with Radiofrequency (RF) energy, sharpened, or otherwise configured to puncture a tissue wall of a hollow body organ or conduit from inside the hollow organ. A user manipulable, proximal end of the guide wire device can remain outside of the patient's mouth or other natural body orifice, e.g., through an endoscopic device as mentioned above. The guide wire device can optionally be configured with a tip that allows axial expansion for passage through tissue. Non-limiting embodiments of guide wire devices are described in more detail in U.S. application Ser. No. 12/427,850 entitled "Methods And Devices For Providing Direction Of Surgical Tools" filed on even date herewith, U.S. Patent Publication No. 2009/0005797 entitled "Methods And Devices For Placement Of An Intra-Abdominal Or Intra-Thoracic Appliance Through A Natural Body Orifice" filed Apr. 22, 2008 and U.S. Patent Publication No. 2009/0018391 entitled "Methods And Devices For Placement Of An Intra-Abdominal Or Intra-Thoracic Appliance Through A Natural Body Orifice" filed Apr. 22, 2008, which are hereby incorporated by reference in their entireties.

Figure 11:
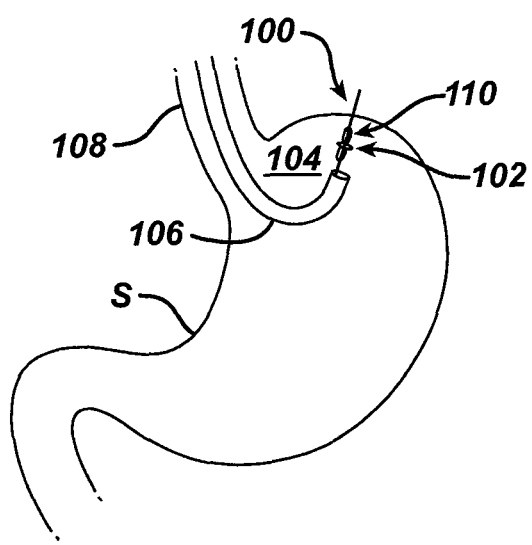
FIG. 11 is a side partially transparent view of one embodiment of a guide wire device positioned through an opening formed in a stomach.

FIG. 11 illustrates one embodiment of a guide wire device 100 forming a hole 102 through a tissue wall 104 of a stomach S. As will also be appreciated by a person skilled in the art, the guide wire device 100 can be introduced into the stomach S of a patient in any way, such as through a working channel of a scoping device 106 inserted through the patient's mouth and through the patient's esophagus 108 as shown in this embodiment. A distal tip 100a of the guide wire device 100 can include a sharpened tip configured to form the hole 102. The guide wire device 100 can optionally include an expandable member in the form of a balloon 110 at a distal end of the device 100 that is configured to allows axial expansion for passage through tissue. In order to create a space to form and/or expand the hole 102, the balloon 110 can be positioned adjacent the tissue wall 104 and/or within the hole 102 and deflated and inflated as often as necessary to accomplish passage through the wall 104. After forming the hole 102 in the tissue wall 104, the guide wire device 100 and/or the scoping device 106 can optionally be removed from the stomach S.

Figure 12:
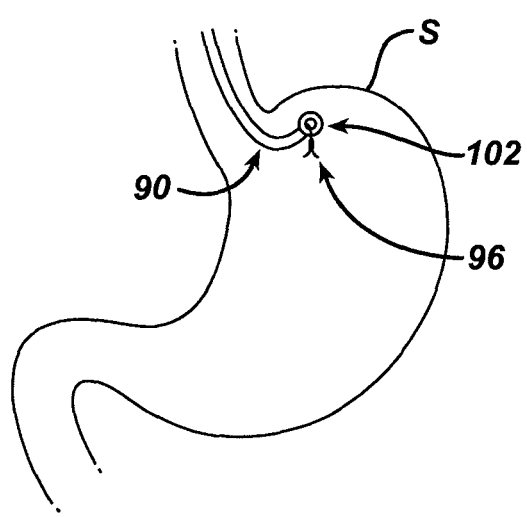
FIG. 12 is a side partially transparent view of the dissection device of FIG. 10 positioned through the opening formed in the stomach of FIG. 11.

In some embodiments, the tissue hole can be formed using a dissecting device, e.g., the dissecting device 10 of FIG. 1, that can be rotated, vibrated axially at audible or sub-ultrasonic frequencies to act similarly to a jack-hammer but at a much smaller scale, and/flexed in one direction and then another at some frequency in order to make passage through the tissue wall possible. If a dissecting device is used to form the hole 102 in the stomach S, the dissecting device can be advanced through the hole 102 with one portion of the device positioned on one side of the tissue wall 104, e.g., inside the stomach S, and a distal-most portion of the device positioned on the other side of the tissue wall 104, e.g., outside the stomach S in the patient's abdominal cavity. Otherwise, a dissecting device, e.g., the dissecting device 90 of FIGS. 9 and 10, can be inserted into the stomach S, e.g., through the mouth and the esophagus 108, and partially through the previously-formed hole 102, as illustrated in FIG. 12, with one portion of the device 90 positioned on one side of the tissue wall 104 and a distal-most portion of the device 90 positioned on the other side of the tissue wall 104. A person skilled in the art will appreciate that the dissecting device 90 can be configured to expand or dilate the tissue opening 102 as the device 90 passes therethrough.

Figure 13:
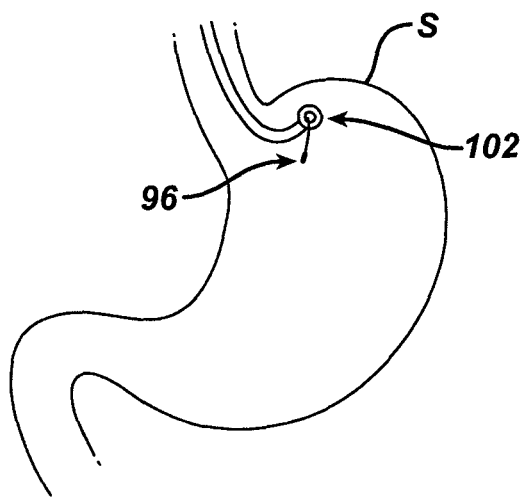
FIG. 13 is a side partially transparent view of the dissection device of FIG. 9 positioned through the opening formed in the stomach of FIG. 11.
Figure 14:
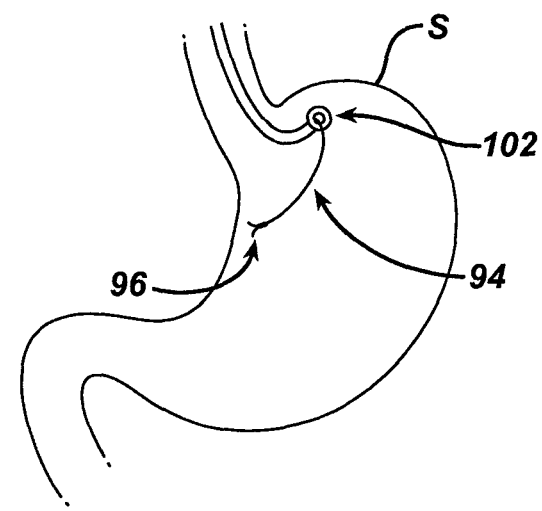
FIG. 14 is another side partially transparent view of the dissection device of FIG. 10 positioned through the opening formed in the stomach of FIG. 11.
Figure 15:
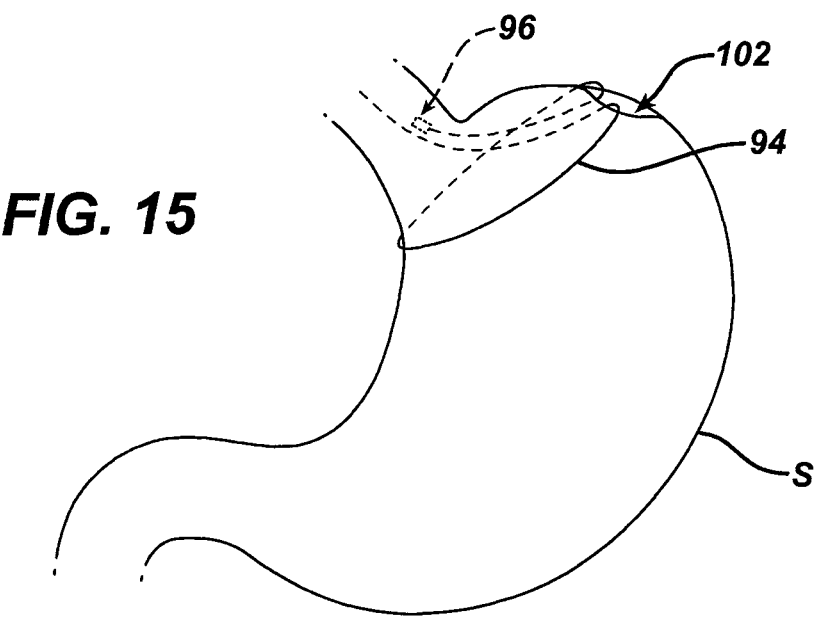
FIG. 15 is a side partially transparent view of one embodiment of the dissection device of FIG. 9 positioned around the stomach of FIG. 11.

By manipulating the proximal handle 92 of the device 90, at least a portion of the elongate shaft 94 of the device 90 can be moved through and outside the wall 104 of the stomach S. As shown in FIGS. 12-14, at least a portion of the elongate shaft 94 can be advanced around at least a partial outer perimeter of the stomach S. The leading end of the device 90, e.g., the shaft's distal-most end or other portion of the device 90 in a distal-most position in the patient's body, can encounter resistance or encounter tissue through which it must pass as it traverses around the stomach S. In that case, the device 90 can be actuated to open and close the jaws 96 to facilitate dissection of the tissue in order to make passage possible, such by actuating a transducer disposed in or otherwise coupled to the device 90 to deliver mechanical energy to the device's elongate shaft 94. The jaws 96 can continuously open and close as the elongate shaft 94 traverses around at least a partial outer perimeter of the stomach S, or the jaws 96 can be selectively opened and closed as tissue to be dissected is encountered. The distal end of the elongate shaft 94 including the jaws 96 can re-enter the stomach S through the hole 102 in the tissue wall 104 or through another opening formed in the tissue wall 104 by the dissecting device 90 and/or one or more other devices. A length of the elongate shaft 94 can thereby be positioned around an outer surface of the patient's stomach S along at least a portion of a perimeter of the stomach S, as shown in FIG. 15, with first and second lengths of the elongate shaft 94 inside the stomach S and a third length of the elongate shaft 94 between the first and second lengths extending at least partially around the perimeter of the stomach S. Throughout such a procedure, at least a portion of the user manipulable, proximal handle 92 can remain outside of the patient's mouth.

The elongate shaft 94 of the device 90 can therefore be configured as a guide wire to allow an implant, such as a restricting band 112, to be advanced over at least a partial length of the elongate shaft 94 to position the band 112 around at least a partial outer perimeter of the stomach S. Alternatively, a guide tube first can be extended over the elongate shaft 94 and the restricting band 112 deployed either inside or outside the guide tube. In some embodiments, the dissecting device 90 can be removed and a restricting band can be placed around the stomach S directly without the need for an additional guide wire or tube, which can be integrated into the band.

Figure 16:
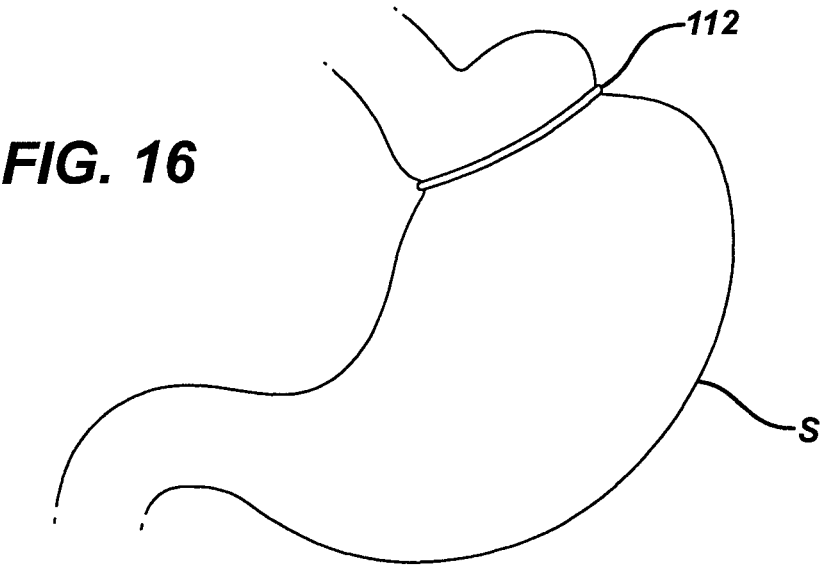
FIG. 16 is a side view of the stomach of FIG. 11 having one embodiment of a restriction band deployed thereon.

Following deployment of the band 112 around the stomach S, the device 90 can be removed from the hole 102, e.g., by proximally moving the device 90, if it has not already been removed, thereby leaving the band 112 in position around the stomach S, as illustrated in FIG. 16. Terminal ends of the band 112 extending into an internal cavity of the stomach S can be tied, crimped, or otherwise joined together, thereby securely positioning the band 112 around at least a partial a circumference of the stomach S. In some embodiments, multiple guide wires and/or dissecting device elongate shafts can be used to deploy the band 112, such as described in more detail in previously mentioned U.S. application Ser. No. 12/427,850 entitled "Methods And Devices For Providing Direction Of Surgical Tools" filed on even date herewith, U.S. Patent Publication No. 2009/0005797 entitled "Methods And Devices For Placement Of An Intra-Abdominal Or Intra-Thoracic Appliance Through A Natural Body Orifice" filed Apr. 22, 2008 and U.S. Patent Publication No. 2009/0018391 entitled "Methods And Devices For Placement Of An Intra-Abdominal Or Intra-Thoracic Appliance Through A Natural Body Orifice" filed Apr. 22, 2008.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing an elongate member into a body of a patient, the elongate member including a first coil disposed in a second coil; and
   actuating a transducer coupled to the elongate member to turn an eccentric wheel to deliver mechanical energy to the elongate member to move at least one of the first and second coils and form a hole through a tissue wall.

2. The method of claim 1, wherein actuating the transducer comprises delivering mechanical energy axially along the elongate member.

3. The method of claim 2, wherein delivering the mechanical energy comprises alternately rotating the elongate member around a longitudinal axis of the elongate member in a first direction and rotating the elongate member around the longitudinal axis of the elongate member in a second direction opposite to the first direction.

4. The method of claim 2, wherein delivering the mechanical energy causes the elongate member to vibrate.

5. The method of claim 1, wherein actuating the transducer comprises delivering mechanical energy to at least one of the first and second coils to move at least one of the first and second coils to form the hole with a distal end of the elongate member.

6. The method of claim 5, wherein delivering mechanical energy to at least one of the first and second coils comprises alternately axially rotating the elongate member in a first direction to tighten the first coil and loosen the second coil and in a second direction to tighten the second coil and loosen the first coil.

7. The method of claim 6, wherein helices of the first coil and the second coil twist in opposite directions.

8. The method of claim 5, wherein delivering mechanical energy to at least one of the first and second coils comprises longitudinally vibrating the first coil relative to the second coil.

9. The method of claim 5, wherein a pair of movable jaws are disposed at the distal end of the elongate member, and wherein delivering mechanical energy to at least one of the first and second coils causes the movable jaws to move and cut the tissue wall.

10. The method of claim 5, wherein a cutting tip configured to dissect tissue is attached to a distal end of the first coil and at least partially extends distally beyond a distal end of the second coil, and wherein delivering mechanical energy to the at least one of the first and second coils causes the cutting tip to move and cut the tissue wall.

11. The method of claim 1, wherein a cutting tip configured to dissect tissue is disposed at the distal end of the elongate member, and wherein delivering mechanical energy to the elongate member causes the cutting tip to move and cut the tissue wall.

12. The method of claim 11, wherein the cutting tip is attached to a distal end of the first coil, and actuating the transducer comprises moving both of the first and second coils to cause the cutting tip to cut the tissue wall.

13. The method of claim 1, wherein advancing the elongate member into the body of the patient comprises advancing the elongate member into the body through a natural orifice of the patient without creating an incision.

14. The method of claim 13, further comprising forming the hole through a wall of a stomach of the patient with a distal end of the elongate member; and
   moving the distal end of the elongate member through the hole to position a first portion of the elongate member inside the stomach and a second portion of the elongate member including the distal end thereof outside the stomach,
   wherein the natural orifice comprises a mouth of the patient,
   wherein advancing the elongate member into the body of the patient comprises positioning a the distal end of the elongate member inside the stomach, and
   wherein delivering the mechanical energy to the elongate member causes the distal end of the elongate member to form the hole through the stomach wall to allow the distal end of the elongate member to be moved through the hole.

15. The method of claim 13, further comprising moving a distal end of the elongate member through the hole to position a first portion of the elongate member inside a stomach of the patient and a second portion of the elongate member including the distal end thereof outside the stomach,
   wherein the natural orifice comprises a mouth of the patient, and
   wherein advancing the elongate member into the body of the patient comprises positioning the distal end of the elongate member inside the stomach.

16. The method of claim 1, wherein the tissue wall comprises a wall of a body lumen.

17. A surgical method, comprising:
   advancing a distal end of an elongate member into a body of a patient, the elongate member being coupled to an eccentric wheel;
   actuating a transducer to deliver electrical energy to the eccentric wheel, thereby turning the eccentric wheel to deliver mechanical energy to the elongate member, the mechanical energy causing an accessory at the distal end of the elongate member to dissect tissue in the body of the patient such that a hole is formed through a tissue wall; and
   moving the distal end of the elongate member through the hole formed through the tissue wall to position first and second portions of the elongate member on opposite sides of the tissue wall.

18. The method of claim 17, wherein the elongate member includes a first coil disposed in a second coil, and wherein actuating the transducer comprises alternately turning the eccentric wheel in a first direction to tighten the first coil and loosen the second coil and turning the eccentric wheel in a second direction to loosen the first coil and tighten the second coil.

19. The method of claim 18, wherein
   the tissue wall comprises a wall of a stomach,
   an accessory attached to a distal end of the first coil dissects the tissue,
   the second portion of the elongate member includes the distal end of the elongate member, and
   after moving the distal end of the elongate member through the hole, the first portion of the elongate member is positioned within the stomach, and the accessory and the second portion of the elongate member are positioned within an abdominal cavity of the patient.

20. The method of claim 17, wherein the eccentric wheel is configured to turn in only one direction such that actuating the transducer turns the eccentric wheel in only the one direction to cause the accessory to dissect the tissue in the body of the patient.

21. The method of claim 17, wherein
the tissue wall comprises a wall of a hollow body organ,
the second portion of the elongate member includes the distal end of the elongate member, and
after moving the distal end of the elongate member through the hole, the first portion of the elongate member is positioned within the hollow body organ, and the second portion of the elongate member is positioned outside the hollow body organ.

* * * * *